(12) United States Patent
Zapletal

(10) Patent No.: US 6,213,967 B1
(45) Date of Patent: Apr. 10, 2001

(54) NECK SUPPORTING DEVICE

(75) Inventor: Jiri Zapletal, Driebergen (NL)

(73) Assignee: World Health Club, S.A., Luxembourg (LU)

( * ) Notice: Subject to any disclaimer, the term of this patent is extended or adjusted under 35 U.S.C. 154(b) by 0 days.

(21) Appl. No.: 09/104,502

(22) Filed: Jun. 25, 1998

(30) Foreign Application Priority Data

Aug. 7, 1997 (NL) .................................................... 1006735

(51) Int. Cl.$^7$ ........................................................ A61F 5/00
(52) U.S. Cl. ..................................... 602/18; 128/DIG. 23
(58) Field of Search ................................. 602/17–19; 2/2, 2/44; 128/DIG. 23

(56) References Cited

U.S. PATENT DOCUMENTS

| | | | |
|---|---|---|---|
| 1,850,660 | * 3/1932 | Coppel | ..................................... 9/345 |
| 3,706,310 | 12/1972 | Garnett . | |
| 3,850,164 | 11/1974 | Hare . | |
| 4,141,368 | * 2/1979 | Meyer | ..................................... 602/18 |
| 4,204,529 | * 5/1980 | Cochrane | ............................... 602/18 |
| 4,757,554 | * 7/1988 | Blair | ............................................ 2/2 |
| 4,794,917 | * 1/1989 | O'leary | ................................... 602/18 |
| 5,056,508 | * 10/1991 | Brunell | .................................... 602/18 |
| 5,395,306 | * 3/1995 | Bauerfeind et al. | ................ 602/19 X |
| 5,409,450 | * 4/1995 | Donelson | ............................... 602/18 |
| 5,551,081 | 9/1996 | Starnes et al. . | |

* cited by examiner

Primary Examiner—Michael A. Brown
(74) Attorney, Agent, or Firm—Akerman Senterfitt

(57) ABSTRACT

A neck supporting device comprises a neck support having two ends which, in use, are positioned at least approximately along the sides of the neck of a user, a waist strap which, in use, extends at least approximately around the waist of the user, and connectors to connect the neck support with the waist strap. In a possible embodiment the connectors comprise two strap portions which, in use, each from a separate end of the neck support, first cross over each other across the chest and then across the back of the user and can be reciprocally fastened at least approximately on the belly, simultaneously forming the waist strap. In another possible embodiment the waist strap is a separate part of the neck supporting device, and the connecting means comprise two strap portions which, each from a separate end of the neck support, can be fastened to the waist strap. The two strap portions can be reciprocally coupled by a clip member which, in use, is positioned at least approximately on the chest of the user.

3 Claims, 3 Drawing Sheets

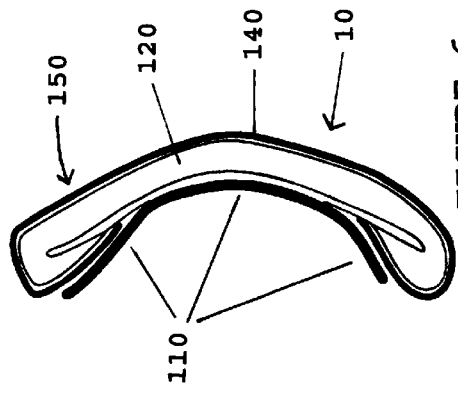
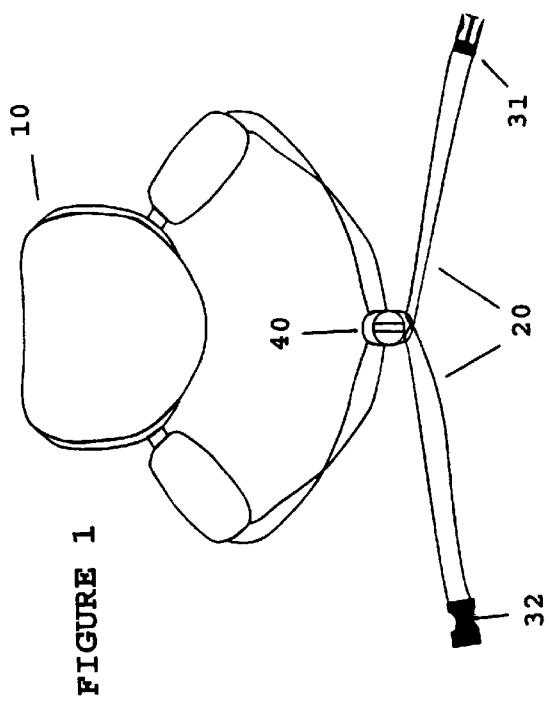
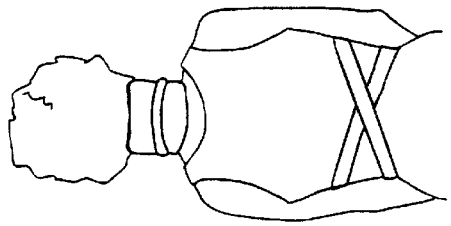
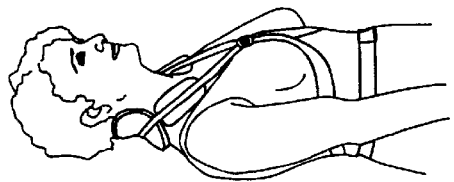
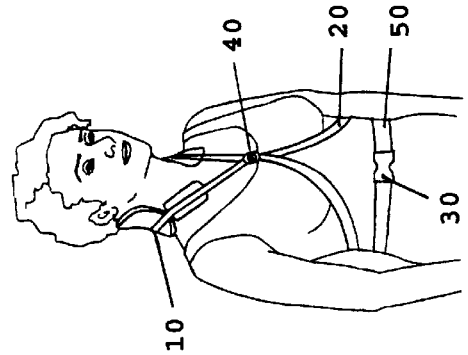

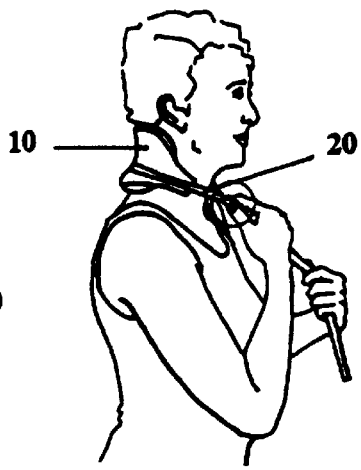
FIGURE 3a        FIGURE 3b
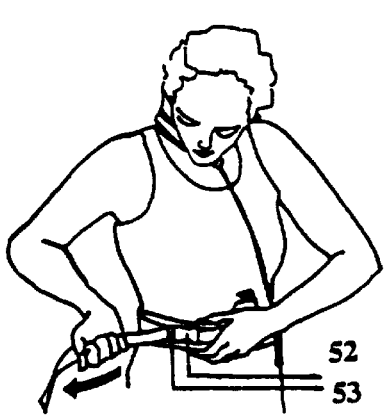
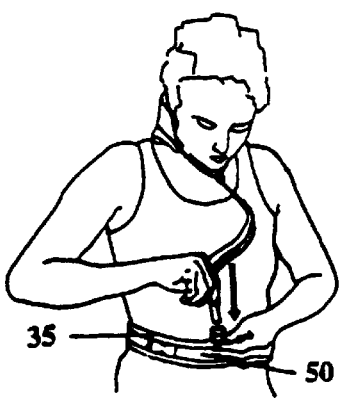
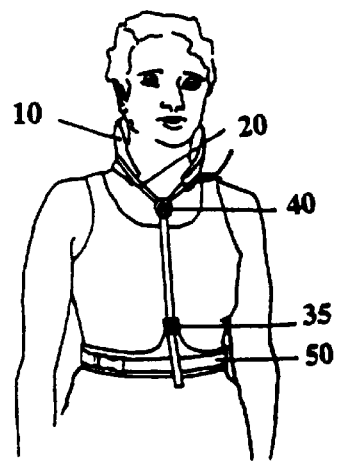
FIGURE 3c      FIGURE 3d      FIGURE 3e

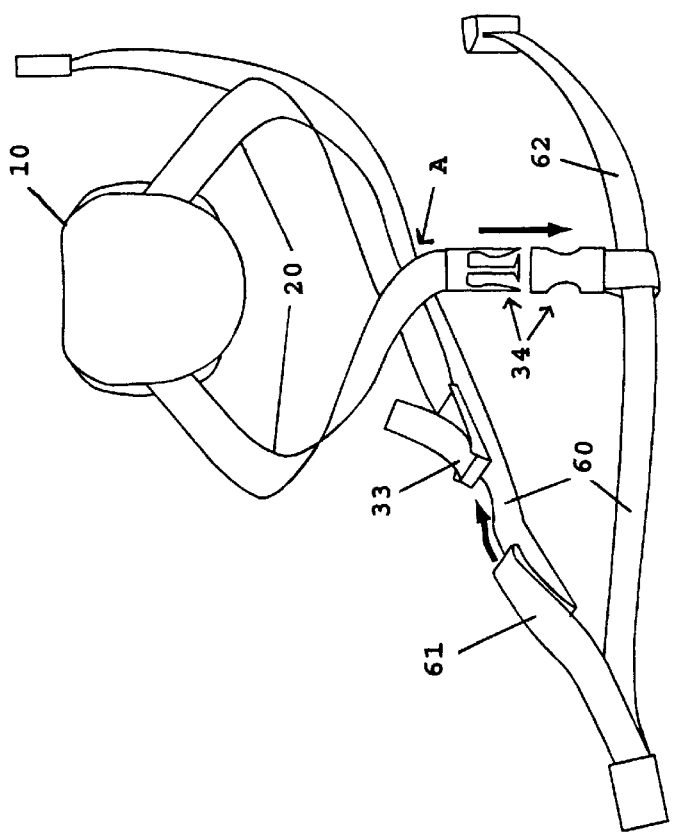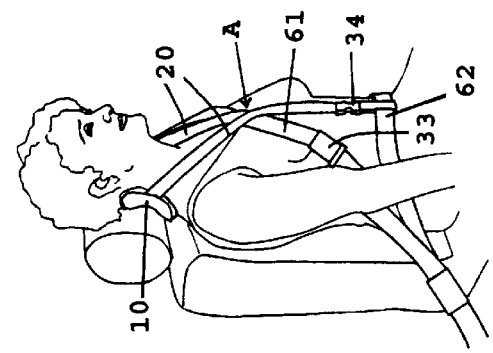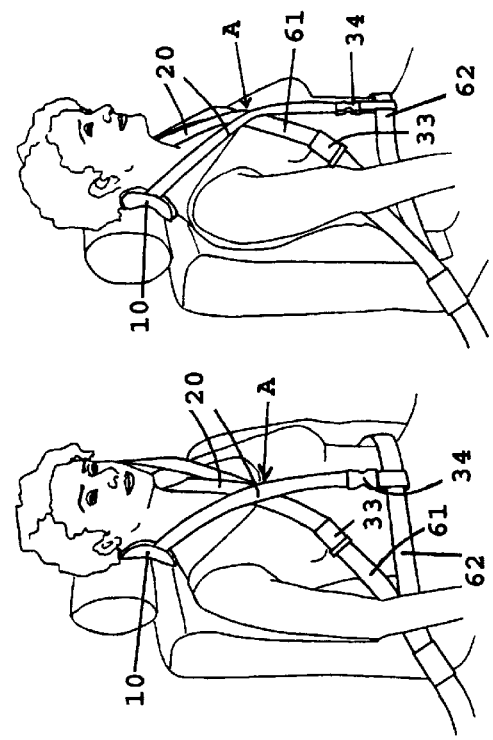
FIGURE 4
FIGURE 5a
FIGURE 5b

NECK SUPPORTING DEVICE

The present invention relates to a neck supporting device.

There are all kinds of situations in everyday life in which the neck of a person can suffer strain. Such a situation may, for instance, occur during a collision between cars, in which a second car collides from the rear with a first car. The passengers of the first car are then at a considerable risk of contracting so-called whiplash. Basically, the body is adjusted to move forward at approximately 5 km per hour. At a movement above 5 km/hour the neck proves to be one of the most vulnerable parts of the human body. The collision from the rear accelerates the forward movement of the car, causing the passengers who are supported by the back rest of the seats also to be accelerated forward. In nearly all cases, however, the back of the head of the passenger is not supported by the back rest or a head rest. Due to the accelerated movement forward of the rest of the person's body the head will now move backward in relation to the body.

During this event great forces are exerted on the neck and the head of the passengers. These forces can cause considerable damage to the neck and head. This damage and the ensuing complaints are called whiplash. Preventing the occurrence of whiplash can avoid much suffering, discomfort and expense.

It is common practice to supply whiplash patients or patients suffering from other neck complaints with a firm, almost completely immobilizing neck collar to be worn around the throat and nape, in order to support the neck. However, this has an adverse effect on, for instance, the joints and muscles in the neck. Studies have shown that complete immobilization is not the proper treatment and than an early mobilization of the neck is very important for a successful treatment of whiplash. Another disadvantage is that such a collar is very much present. Thereby a patient's infirmity becomes obvious to his surroundings and his privacy is harmed.

Another situation in which a person's neck may be strained is when working behind a (computer) screen. This causes fatigue symptoms of the neck which after some time may lead to complaints requiring treatment. If these fatigue symptoms can be avoided, the complaints requiring treatment will also not occur.

There are known neck supporting devices in use, in which the neck support is held against the neck by means of straps which run from the neck, under the armpits to the back of a user. With such devices the throat is also enveloped for a large part, resulting in extensive immobilization of the neck, throat and head. In order to hold the neck/throat support firmly and supportingly against the body a considerable force has to be exerted on the straps. This means that a pressure is applied to the soft body parts of the throat, which is uncomfortable and may be harmful. The force exerted on the neck supporting device is further directed mainly to the sides of the user's body and not to the front, as would be desirable for proper support to the neck. Moreover, the configuration of these known devices results in a constricting pressure around the chest and under the armpits.

It is the object of the invention to solve the problems described above. To this end the invention provides a neck supporting device, comprising a neck support having two ends which, in use, are positioned at least approximately along the sides of the neck of a user, a waist strap which, in use, extends at least approximately around the waist of the user, and connecting means to connect the neck support with the waist strap.

Such a neck supporting device provides a good support to the neck and makes it possible that only a rearward movement of the neck is restricted without restricting other movements of the head and without any pressure on the throat.

In a preferred embodiment the connecting means comprise two strap portions which, in use, each from a separate end of the neck support, first cross over each other across the chest and then across the back of the user and can be reciprocally fastened at least approximately on the belly, simultaneously forming the waist strap. For a simple and quick fastening it is preferred that the strap portions of such an embodiment can be reciprocally fastened by means of a coupling device at least approximately on the belly of the user.

In another preferred embodiment the waist strap is a separate part of the neck support device, and the connecting means comprise two strap portions which, each from a separate end of the neck support, can be fastened to the waist strap. For a quick and simple fastening it is preferred that the two strap portions can be fastened to the waist strap jointly. To further improve the fastening it is preferred that the strap portions can be fastened to the waist strap by means of a coupling device.

In a favourable embodiment the tension in the strap portions is variable by means of an adjustment device, so that the force by which the neck support is held against the neck, and consequently the degree of possible rearward movement of the neck, can be varied.

In a particularly favourable embodiment the two strap portions can be reciprocally coupled by means of a clip member which, in use, is positioned at least approximately on the chest of the user. Such a clip member further improves the stability of the neck supporting device around the body of the user.

The clip member is preferably slidable over the strap portions. By sliding the clip member the course of the strap portions across the user and the forces exerted on the neck and/or throat of the user can then be varied as desired. In order to avoid unintended sliding of the clip member during use, it is preferable that the clip member can be fixed on the strap portions.

In order to ensure that the neck support retains its shape, it is preferred that the rear side of the neck support facing away from the body comprises a firm, flexible material. Due to this material the neck support will now provide optimal support to the neck while being able to adapt to the shape of the neck and the body movements.

It is preferred that the front side, rear side and upper side of the neck support coming into contact with the body, comprise a soft foam material. The neck support is thus able to adapt better to the shape of the neck and the head, and is extremely comfortable to wear.

In an advantageous embodiment the shape of the neck support is adapted to that of the neck. This shape further improves the supporting ability and comfort of the neck support.

It is preferred that the neck support is enveloped by a covering of textile material such as possibly towelling cotton. This material makes the feel of the neck support extremely comfortable during use and will not irritate the skin.

In a convenient embodiment the covering is in addition removable by means of closure means provided in the covering. This allows the covering surrounding the neck support to be removed for cleaning. It is also possible to use coverings of different color and/or pattern, for instance a color going with the clothing in order to render the device as inconspicuous as possible.

The closure means may be synthetic materials which adhere when pressed together, commonly sold under the trade name of VELCRO fastening or a zipper, which provide an efficient closure of the covering.

BRIEF DESCRIPTION OF THE DRAWINGS

The invention will now be elucidated with reference to the accompanying drawing in which similar parts are indicated by the same reference numbers. In the drawing:

FIG. 1 shows a first embodiment of the neck supporting device according to the invention;

FIGS. 2a, 2b and 2c show a schematic front view, side view and rear view respectively of the neck supporting device according to FIG. 1, as fitted on a user;

FIGS. 3a, 3b, 3c 3e and 3d show how a second embodiment of the neck supporting device according to the invention is fitted on a user; and FIG. 4 shows a schematic cross section of a neck support according to the invention.

DETAILED DESCRIPTION OF THE PREFERRED EMBODIMENTS

The first embodiment of the neck supporting device according to the invention shown in FIG. 1 comprises a back support 10 and two strap portions 20 each attached to a different end of the neck support 10. One end of the strap portions 20 is attached to the neck support 10 and their other end can be reciprocally coupled by means of a coupling device 30, such as a buckle. It is also possible that the strap portions 20 are formed by a single strap positioned around the neck support. This strap can be attached to the neck support at one single point, such as in the middle of the rear side, or at different points, such as at the ends. The strap could also be positioned around the neck support without being attached.

In the embodiment shown, each of the ends of the strap portions 20 which can be reciprocally coupled, is provided with the, as such known, buckle parts 31, 32 which can be coupled to form a buckle 30. It is also easy to undo this buckle 30 again. The neck supporting device according to the invention further possesses a clip member 40, reciprocally coupling the crossing strap portions 20.

FIG. 2 shows the neck supporting device of FIG. 1 fitted on a user. During fitting the head is passed through the opening formed by the neck support 10, the strap portions 20 and the clip member 40. The neck support 10 is applied on the shoulders and against the neck of the user, after which the strap portions 20 are guided over the chest, behind the back and over the belly of the user. At the belly the strap portions 20 are coupled by means of the buckle 30. The strap portions 20 now also form a waist strap 50.

After coupling, the strap portions 20 may be tightened by pulling at the end of a strap portion 20, which strap portion end 20 is fed through an adjustment device (not shown, but known as such), which is configured as a feed-through device and which is attached to the buckle. To allow the neck supporting device to be pulled tightly around the body, the strap portion 20 can slide through said feed-through device in a first direction, whereas it cannot slide through in the other direction. When the buckle 30 is uncoupled, the strap portion 20 can slide through said feed-through device in a first direction. When the buckle 30 is uncoupled, the strap portion 20 can also slide in the other direction. The adjustment device may be provided at one or at both buckle parts 31, 32. A buckle with the above-mentioned adjustment device is known as such.

It is also possible to use another kind of buckle, such as a buckle which is attached to one strap portion only and through which the other strap portion is fed, coupling being effectuated by means of a tongue of the buckle which is inserted into an opening in the other strap portion. The provision of a number of openings in the other strap portion allows the neck supporting device to be fitted tighter or more loosely. However, many other embodiments of buckle couplings are feasible. It is also possible to couple the two strap portions by means of a VELCRO fastening or by means of a knot.

The second embodiment of the neck supporting device according to the invention shown in FIGS. 3a to 3e also comprises a neck support 10 and a strap positioned around the neck support 10, which strap is attached (not shown) to the ends and the rear middle of the neck support 10. This results in two strap portions 20, each of which is attached to a different end of the neck support. In the embodiment shown, said strap portions 20 are fed through a clip member 40. The neck support 10 with the strap portions 20 and the clip member 40 according to the second embodiment, are fitted on a user in a similar manner as in the first embodiment.

In the application of this embodiment as shown in FIG. 3e the ends of the strap portions 20 facing away from the neck support, are attached to the waist strap 50 by means of a coupling device 35. This coupling device 35 may be a buckle, but is in the embodiment shown configured as a feed-through device, which also serves as an adjustment device by which the two strap portions 20 may be tightened between the neck support 10 and the waist strap 50. The two strap portions 20 extend, bundled together, between the clip member 40 and the waist strap 50.

The waist strap 50 may be a trouser belt to which a (part of a) coupling device for the strap portions 20 is attached. In the embodiment shown in FIGS. 3a to 3e the waist strap 50 is formed by a strap having two ends which can be coupled by means of a buckle 52. To the buckle 52 an adjustment device 53, which is configured as a feed-through device, is attached for tightening the waist strap 50.

The clip member 40 through which the two strap portions 20 are fed, can slide over the strap portions 20 of the two embodiments shown. This slidable clip member 40 allows adjustment of the course of the strap portions 20 over the chest of the user. The more the clip member 40 is slid toward the neck support 10, the firmer the neck support will fit around the neck of the user. The position of the clip member 40 may be varied as required. In order to keep the clip member 40 in a chosen position on the strap portions 20, it may be fixed on the strap portions 20 by means which are not shown.

The shape of the neck support 10 is preferably adapted to that of the neck, the shoulders and the head, as can be seen in FIG. 1, and the front-, upper- and underside coming into contact with the body, are made from a soft foam material 110, as shown schematically in FIG. 4. It is preferred that the rear side of the neck support 10 comprises a firm, flexible material 120. This will ensure that the neck support 10 provides optimal support and will be comfortable to wear. The strap portions 20 are attached to the firm, flexible material 120. FIG. 4 shows a possible schematic cross section of the neck support 10 according to the invention.

The neck support 10 may be enveloped by a first material layer 130 of, for instance, cotton. It is preferred that there be a second material layer 140 of a textile material such as towelling with a pleasant feel to the skin. In a preferred embodiment said second layer 140 is provided with a closure means 150, such as a zip or a Velcro fastening, to allow the second layer to be removed and changed. This makes it possible to clean the second layer 140 and to choose the second layer 140 in a color and pattern to go with the clothing of the user.

The embodiments of the neck supporting device according to the invention shown can be fitted on the body of a user easily and within a few seconds. In addition, they can be adjusted to the individual user.

A big advantage of the neck supporting device according to the device is the great degree of freedom of movement, restricting everyday activities as little as possible and supporting the neck in the correct manner to ensure a successful treatment of whiplash. In addition, said neck supporting device is virtually inconspicuous and may be disguised completely, for instance, by wearing a shawl.

The neck supporting device according to the invention affords excellent protection against incidents in which straining of the head and neck may occur, such as in a car collision from the rear (whiplash). The device may be applied as preventive means against injury of this kind, but also as a support for people suffering from existing neck complaints stemming, for instance, from a whiplash and other strains, from a neck hernia or a neck sprain, after a neck hernia operation, for the treatment of neck injury and degeneration (arthrosis), etc.

The embodiments described above are not to be understood as limiting the invention. The neck supporting device may be realized in a variety of embodiments, all deemed to be within the scope of the appended claims.

What is claimed is:

1. A neck supporting device, comprising:

a neck support having two ends, said neck support including a semi-rigid member having a curvature adapted to be positioned adjacent the back and the sides of the neck of a user;

a waist strap which, in use, extends at least approximately around the waist of the user;

connecting means connecting the neck support with the waist strap;

wherein the connecting means comprises two strap portions which, in use, from a separate end of the neck support, first cross over each other across the chest and then across the back of the user and can be reciprocally fastened at least approximately on the belly of the user, simultaneously forming the waist strap; and wherein the two strap portions can be reciprocally coupled by means of a clip member which, in use, is positioned at least approximately on the chest of the user.

2. A neck supporting device according to claim 1, wherein the clip member is slidable over the strap portions.

3. A neck supporting device according to claim 2, wherein the clip member can be fixed on the strap portions.

* * * * *